(12) United States Patent  
Slutsky et al.

(10) Patent No.: US 9,280,815 B2  
(45) Date of Patent: Mar. 8, 2016

(54) COMPARISON WORKFLOW AUTOMATION BY REGISTRATION

(75) Inventors: Michael Slutsky, Kfar-Saba (IL); Shmuel Akerman, Binyamina (IL); Reuven Shreiber, Haifa (IL)

(73) Assignee: Algotec Systems Ltd., RaAnana (IL)

( * ) Notice: Subject to any disclaimer, the term of this patent is extended or adjusted under 35 U.S.C. 154(b) by 1368 days.

(21) Appl. No.: 12/516,217

(22) PCT Filed: Nov. 22, 2007

(86) PCT No.: PCT/IL2007/001443  
§ 371 (c)(1),  
(2), (4) Date: Jan. 21, 2010

(87) PCT Pub. No.: WO2008/062415  
PCT Pub. Date: May 29, 2008

(65) Prior Publication Data  
US 2010/0235352 A1   Sep. 16, 2010

(30) Foreign Application Priority Data  
Nov. 26, 2006   (IL) .......................................... 179582

(51) Int. Cl.  
*G06K 9/00* (2006.01)  
*G06T 7/00* (2006.01)  
*G06T 19/00* (2011.01)  
*G06F 19/00* (2011.01)

(52) U.S. Cl.  
CPC ............... *G06T 7/0012* (2013.01); *G06T 19/00* (2013.01); *G06F 19/321* (2013.01); *G06T 7/0081* (2013.01); *G06T 7/0083* (2013.01); *G06T 2207/30004* (2013.01); *G06T 2210/41* (2013.01)

(58) Field of Classification Search  
CPC ... G06T 7/0012; G06T 19/321; G06T 7/0083; G06T 2207/30004; G06T 7/0081; G06T 3/0481; G06T 2203/04806; G06T 3/04845; G06T 3/0485; G06T 3/04855; G06T 17/30864; G06T 17/30867; G06T 30/02; G06T 17/30675; G06T 17/30696  
USPC .......... 707/803, 723, 769, 802; 382/128, 134, 382/171, 131; 345/424, 435, 441, 442; 600/426, 425  
See application file for complete search history.

(56) References Cited

U.S. PATENT DOCUMENTS 5,769,789 A  *  6/1998  Wang ..................... A61B 19/52  
                                              382/131  
5,954,650 A     9/1999  Saito et al.  
(Continued)

FOREIGN PATENT DOCUMENTS

EP       1336376        8/2003  
WO    WO 2008/062415    5/2008

OTHER PUBLICATIONS

Communication Relating to the Results of the Partial international Search Dated Jun. 2, 2008 From the International Searching Authority Re.: Application No. PCT/IL2007/001443.  
(Continued)

*Primary Examiner* — Abderrahim Merouan

(57) ABSTRACT

A method for a rapid automated presentation of at least two radiological data sets of a patient, comprising, (a) automatically registering the data sets in 3D space; and (b) concurrently presenting substantially matching anatomical regions in each data set.

26 Claims, 7 Drawing Sheets

(56) References Cited

U.S. PATENT DOCUMENTS

| | | | | |
|---|---|---|---|---|
| 6,003,043 | A * | 12/1999 | Hatakeyama et al. | 1/1 |
| 2004/0122790 | A1* | 6/2004 | Walker et al. | 707/1 |
| 2004/0184647 | A1* | 9/2004 | Reeves et al. | 382/131 |
| 2005/0033523 | A1* | 2/2005 | Abe et al. | 702/20 |
| 2005/0111757 | A1* | 5/2005 | Brackett et al. | 382/294 |
| 2005/0232474 | A1* | 10/2005 | Wei et al. | 382/128 |
| 2006/0008143 | A1* | 1/2006 | Truyen et al. | 382/173 |
| 2006/0206527 | A1* | 9/2006 | Hattori | 707/104.1 |
| 2007/0047840 | A1* | 3/2007 | Xu et al. | 382/294 |
| 2007/0110289 | A1* | 5/2007 | Fu et al. | 382/128 |
| 2007/0118399 | A1* | 5/2007 | Avinash et al. | 705/2 |
| 2009/0290771 | A1* | 11/2009 | Frank et al. | 382/128 |
| 2009/0324041 | A1* | 12/2009 | Narayanan et al. | 382/131 |
| 2010/0069742 | A1* | 3/2010 | Partain et al. | 600/424 |
| 2010/0272330 | A1* | 10/2010 | Pekar et al. | 382/128 |
| 2010/0329529 | A1* | 12/2010 | Feldman et al. | 382/131 |
| 2011/0103664 | A1* | 5/2011 | Kovalski | 382/131 |

OTHER PUBLICATIONS

Communication RElating to the Results of the Partial International Search Dated May 13, 2008 From the International Searching Authority Re.: Application No. PCT/IL2007/001443.
International Search Report Dated Feb. 3, 2009 From the International Searching Authority Re.: Appllication No. PCT/IL2007/001443.
Written Opinion Dated Feb. 3, 2009 From the International Searching Authority Re.: Application No. PCT/IL2007/001443.
Claessens et al. "Non-Rigid Image Registration for Temporal Subtraction of Whole-Body Nuclear Emission Images", IEEE Nuclear Sience Symposium Conference Record, XP002508321, 5: 3173-3175, Oct. 2003. p. 3173-3174.
Hadjiiski et al. "Automated Registration of Breast Lesions in Temporal Pairs of Mammograms for Interval Change Analysis—Local Affine Transformation for Improved Localization", Medical Physics, XP012011481, 28(6): 1070-1079, Jun. 2001. Figs.1-7, Section II.
Lester et al. "A Survey of Hierarchical Non-Linear Medical Image Registration", Pattern Recognition, XP004151619, 32(1): 129-149, Jan. 1999. Section 3.3, Sections 3.1.1-3.1.5.
Pham et al. "Current Methods in Medical Image Segmentation", Annual Review of Biomedical Engineering, XP009062827, 2: 315-337, Aug. 1, 2000. p. 327-331.
Sanjay-Gopal et al. "A Regional Registration Technique for Automated Interval Change Analysis of Breast Lesions on Mammograms", Medical Physics, XP012010682, 26(12): 2669-2679, Dec. 1999. Section II.A, Figs.1-3.
Thevenaz et al. "A Pyramid Approach to Subpixel Registration Based on Intensity", IEEE Transactions on Image Processing, XP002326692, 7(1): 27-41, Jan. 1998. Sections III, IV, VIII, Abstract.
Wong et al. "Efficient Multi-Modal Least-Squares Alignment of Medical Images Using Quasi-Orientation Maps", Proceedings of the International Conference on Image Processing and Computer Vision (IPCV '06), XP002508322, p. 74-80, Jun. 2006.
Decision to Refuse a European Patent Application (Art. 97(2) EPC) Dated May 31, 2011 From the European Patent Office Re. Application No. 07827416.4.
Response Dated Sep. 28, 2011 to Decision to Refuse a European Patent Application (Art. 97(2) EPC) of May 31, 2011 From the European Patent Office Re. Application No. 07827416.4.
Summons to Oral Proceedings Pursuant to Rule 115(1) EPC Dated Oct. 8, 2012 From the European Patent Office Re. Application No. 07827416.4.
Communication Pursuant to Article 94(3) EPC Dated Jul. 14, 2010 From the European Patent Office Re. Application No. 07827416.4.
Response Dated Dec. 1, 2010 to Communication Pursuant to Article 94(3) EPC of Jul. 14, 2010 From the European Patent Office Re. Application No. 07827416.4.
Response Dated Apr. 17, 2011 to Summons to Attend Oral Proceedings Pursuant to Rule 115(1) EPC of Feb. 9, 2011 From the European Patent Office Re. Application No. 07827416.4.
Summons to Attend Oral Proceedings Pursuant to Rule 115(1) EPC Dated Feb. 9, 2011 From the European Patent Office Re. Application No. 07827416.4.
Communication Pursuant to Article 94(3) EPC Dated Mar. 27, 2014 From the European Patent Office Re. Application No. 07827416.4.

* cited by examiner

COMPARISON WORKFLOW AUTOMATION BY REGISTRATION

RELATED APPLICATIONS

This application is a National Phase of PCT Patent Application No. PCT/IL2007/001443, filed on Nov. 22, 2007, which claims priority from Israeli Patent application No. 179582, filed on Nov. 26, 2006, and entitled "Comparison workflow automation by registration", the disclosure of which is herein incorporated by reference.

FIELD OF THE INVENTION

The present invention relates to the registration and manipulation of radiological scans. Some embodiments relate to automatic registrations of partially overlapping CT, MRI, US, PET or SPECT scans.

BACKGROUND OF THE INVENTION

A cornerstone of radiological diagnostics is a comparison of current examination with prior ones. The usage of complementary examinations e.g. PET-CT for metabolic and anatomic information, MRI (good contrast resolution) and CT (good spatial resolution and detection of calcifications) is also widely spread.

A partial list of procedures where two or more data sets are used for diagnosis:
1. Tumor management (inter and intra modality)
   a. Tumor (type) analysis (are there calcification, hemorrhage, etc.)
   b. Treatment efficiency and growth assessment
2. Lymph nodes follow-up (PET-CT)
3. Trauma follow-up (e.g. clearance of intracranial hemorrhage).
4. Brain stroke management (CT-MRI)
5. Spine disk disease MRI and CT and follow-up
6. Knee imaging—MRI and CT
7. Pre and post operation follow-up e.g. evacuation of inflammatory collections.

For efficient usage of multiple data sets of the same pathology in current common visualization tools the data sets must agree almost exactly in spatial scan parameters e.g. orientation of plane of cross section, spacing between slices, thickness and in-plane resolution. However, examinations taken at different time, locations and source modality tend to differ in spatial parameters.

Typical reading workflow includes examining the current data set, comparing the assessment results to the prior and complementary data sets, taking measurements of pertinent features and reporting the findings and results. In majority of examinations the tools that are used are merely adjustments of imaging parameters (e.g. zoom and window level) hence most of the time is spent on actual diagnosis and not on manipulation of the data. State of the art reading applications supply sophisticated tools for manipulating a single data set. The work load of manually adjusting the data sets puts a significant damper on the reading process and may prevent meticulous comparison or efficient use of complementary data sets. A procedure that can facilitate a reliable diagnosis when the orientation or pixel spacing of two data sets is dissimilar includes volumetric registration (matching) of the data sets. Presently, this procedure is limited in use to dedicated post-processing workstations only, where an intervention of the operator is usually required, resulting in a lengthy operation and low reproducibility since it relies on a manual operation. Thus, it is not considered suitable for the demands of a routine high-throughput radiology diagnostics.

SUMMARY OF THE INVENTION

A broad aspect of some embodiments of the invention relates to unified multiple data set manipulation. Optionally, the manual operation complexity is on the order experienced in zoom or window level adjustment. Potential advantages of some implementations of the invention include that such procedures may be very fast, reliable, require minimal user intervention and/or can be incorporated into the routine workflow of reading and reporting.

An aspect of some embodiments the invention relates to an automated and/or rapid presentation and/or comparison between radiological data sets, allowing a radiologist to compare respective anatomical regions concurrently on a standard radiology reading workstation.

In some exemplary embodiments of the invention, a workstation is used to load at least two data sets (CT, MRI, PET, SPECT or US) of a patient and to register their three-dimensional (3D) volumes so that the spatial positions of respective anatomic points, in a substantial portion in each volume of a data set, are similar.

In the application and claims, the terms 'volume matching' and '3D registration' of data sets (or their inflections) are equivalent and will be used interchangeably. In an exemplary embodiment of the invention, the total time for reading procedures utilizing automatic volume matching is not substantially influenced and typically reduced compared to procedures without volume matching. In some cases, the registered data sets may facilitate a better and/or more reliable diagnosis with possibly reduced effort on behalf of the radiologist.

Optionally at least one data set is retrieved automatically. Optionally the data sets for registration are selected automatically. Optionally the registration is activated automatically, for example, based on availability or based on user preference or clinical procedure.

In some exemplary embodiments of the invention, the quality of the spatial registration is assessed. Optionally, the assessment is invoked automatically.

In some exemplary embodiments of the invention, registered data sets are presented simultaneously on a radiology workstation in multi-planar format along the same axis, or as a rendered volume. The data sets may be at least partially overlaid or merged with each other. The volumes may be viewed in a synchronized manner, for example, when scrolling through the planes of one data set, the respective planes at another data set are presented. Likewise, an operation that is performed at or on a point in a data set may be applied at a corresponding point in another data set accordingly. Optionally the access and/or manipulation of two volumes is simultaneous.

In some exemplary embodiments of the invention, the registration may relate to only a certain portion of the volume, for example to eliminate irrelevant parts that may consume processing time and/or parts that are deformed or such that they will hamper the registration or lead to inappropriate registration.

In some exemplary embodiments of the invention the registered data sets may be stored for subsequent retrieval as pre-registered data sets.

An aspect of some embodiments the invention relates to a method for volume matching that takes into account the fact that the patient being imaged, has a disease. In an exemplary embodiment of the invention, certain anatomical structures, regions and/or types of structures are given precedence over other ones to determine the degree of the spatial matching. Alternatively or additionally, an expected amount of movement of some structures is assumed and/or allowed due to the disease.

The matching is optionally based on the contribution of pixels or voxels values to a cost function. For example, when data sets of different stages of a disease that affects bodily features are matched, the skeleton elements at a particular region and posture, which typically do not change substantially between the scans, are given larger weight relative to the soft tissues at those locations, as they may vary between scans due to the disease. As another example, a certain region of interest may take precedence over other regions so that that region contributes more than others to the determination of the spatial match or of the registration algorithm. In another example, distortion of brain tissue to a tumor growth is allowed, and registration will focus on the tumor, rather than the surrounding and displaced brain tissue.

An aspect of the invention relates to a method for rapid registration of partially overlapping scans, employing stepwise intermediate matching steps on a series of data sets having reduced resolutions to varying degrees, where the data sets are ordered by the spatial or contrast resolution ('pyramid'). Optionally, a coarse match is obtained relatively fast (with respect to a more refined operation) in the initial stages of the procedure, followed by refinements to a specified or determined level. In an exemplary embodiment of the invention, the matching method and/or parameters applied at different levels are different. For example, the number and/or type of degrees of freedom allowed at a lower resolution level can be different than at a higher resolution level. In an exemplary embodiment of the invention, for lower resolutions translation is applied and for higher resolutions rotation is applied as well. Alternatively or additionally, the number of translational and/or rotational degrees of freedom is varied. Alternatively or additionally, scaling in one or more dimensions is applied only at some resolution levels. Optionally, a higher resolution level assumes a transformation value provided by a lower resolution level.

An aspect of some embodiments the invention relates to a local refinement of the spatial registration of previously registered data sets. Optionally, the refinement is performed in order to evaluate pathologies in soft tissues, for example, to compare growth and/or relapse of tumors between two data sets. In some cases, the soft tissues and/or pathologies are not present, or are not properly matched, in corresponding volumes of two or more data sets after a global registration (which might have a bias for particular anatomies such as bones). Optionally, a fine matching (registration refinement) is used to find the corresponding region of interest of the soft tissues in each data set.

In exemplary embodiments of the invention, the data sets are globally registered by one or more of the methods as described above, e.g., based on skeleton.

Subsequently, in exemplary embodiments of the invention, a volume in one data set is selected and a corresponding volume in one or more data sets is automatically determined. Optionally, the determination comprises a matching as described above. Optionally, the determination comprises a step-wise matching on a pyramid of increasing resolutions as described above. Optionally, the voxels are given the same relative weight.

In exemplary embodiments of the invention, the refinement comprises identifying a characteristic zone (or point) in one data set and determining a corresponding zone (or point) in one or more other data sets. Optionally, the determination is performed by successive steps, each step improving the matching, until the refinement converges to a sufficient match (optionally up to a limit on the number of steps). Optionally, in each step the sub-volume (section) about the matched zones is reduced for better matching.

In exemplary embodiments of the invention, the local refinement depends on one or more conditions: (a) the global registration is successful (e.g. by bones), (b) the soft tissue (ROI) volume and shape are similar between globally registered data sets, and (c) the location of soft tissues in the globally registered data sets is about the same (e.g. moved due to breathing, but bowels or stomach may be precluded due to large motions between scan).

In exemplary embodiments of the invention, the fine-matched sections, or the respective transformation, are stored for later analysis, optionally saving the need for repeating the pathology identification and/or registration refinement or as a starting point for such.

There is thus provided in accordance with an exemplary embodiment of the invention a method for a rapid automated presentation of at least two radiological data sets of a patient, comprising:

(a) automatically registering the data sets in 3D space; and (b) concurrently presenting substantially matching anatomical regions in each data set. Optionally, the presentation is performed on a radiological reading workstation suitable for high-throughput radiological display. Alternatively or additionally, the time required for the presentation is of the order of or less than the time required to retrieve the data sets. Alternatively or additionally, at least one data set is retrieved automatically. Alternatively or additionally, the registration is activated automatically. Alternatively or additionally, the activation of registration is configurable.

Optionally, the method comprises:

(a) assessing the quality of the spatial registration; and (b) reporting a score for the registration quality.

In an exemplary embodiment of the invention, the registered data sets are presented in a multi-planar format, the planes arranged substantially along the same spatial axis.

In an exemplary embodiment of the invention, the registered data sets are presented as rendered volumes.

In an exemplary embodiment of the invention, the registered data sets are at least partially merged with each other for presentation.

In an exemplary embodiment of the invention, the method comprises:

(a) manipulating one data set; and (b) automatically applying the manipulation to a substantially corresponding location in another co-displayed data set.

In an exemplary embodiment of the invention, the method comprises a manual intervention for registration after said automatic registration.

In an exemplary embodiment of the invention, the method comprises selecting in at least one volume a participating portion that will take part in the registration.

In an exemplary embodiment of the invention, the participation portion is determined automatically.

In an exemplary embodiment of the invention, the participation portion is selected manually.

There is also provided in accordance with an exemplary embodiment of the invention, a method of volume matching at least two radiological data sets of a patient, comprising:

(a) providing at least two data sets comprising 3D data, each data set including voxels representing at least two tissue types; and (b) determining a matching while giving greater weight to matching between voxels of one tissue type than of another tissue type. Optionally, said two tissue types include at least one bone tissue which is given greater weight. Alternatively or additionally, the method comprises a manual determination of at least one tissue type. Alternatively or additionally, at least one tissue type is identified by structure.

There is also provided in accordance with an exemplary embodiment of the invention a method of spatially matching volumes of radiological data sets, comprising:

(a) processing the volumes to yield a series of volumes in decreasing resolution; and (b) repeatedly performing consecutive stepwise volumetric spatial matching on the processed volumes, the resolution increasing at each step, said spatial matching employing a selective combination of degrees of freedom for each step. Optionally, a lower resolution volume is spatially matched using translation and at least one higher resolution volume is spatially matched using rotation and translation.

There is provided according to any of the preceding methods, a method where at least one region of interest is stored in a data structure configured for a subsequent fast browsing. Optionally, the data structure is configured for a subsequent local registration refinement.

There is also provided in accordance with an exemplary embodiment of the invention, apparatus configured to carry out the method of any of the above claims and including a programmable computer.

BRIEF DESCRIPTION OF THE DRAWINGS

Exemplary non-limiting embodiments of the invention described in the following description, read with reference to the figures attached hereto. In the figures, identical and/or similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF EMBODIMENTS OF THE INVENTION

Figure 1:
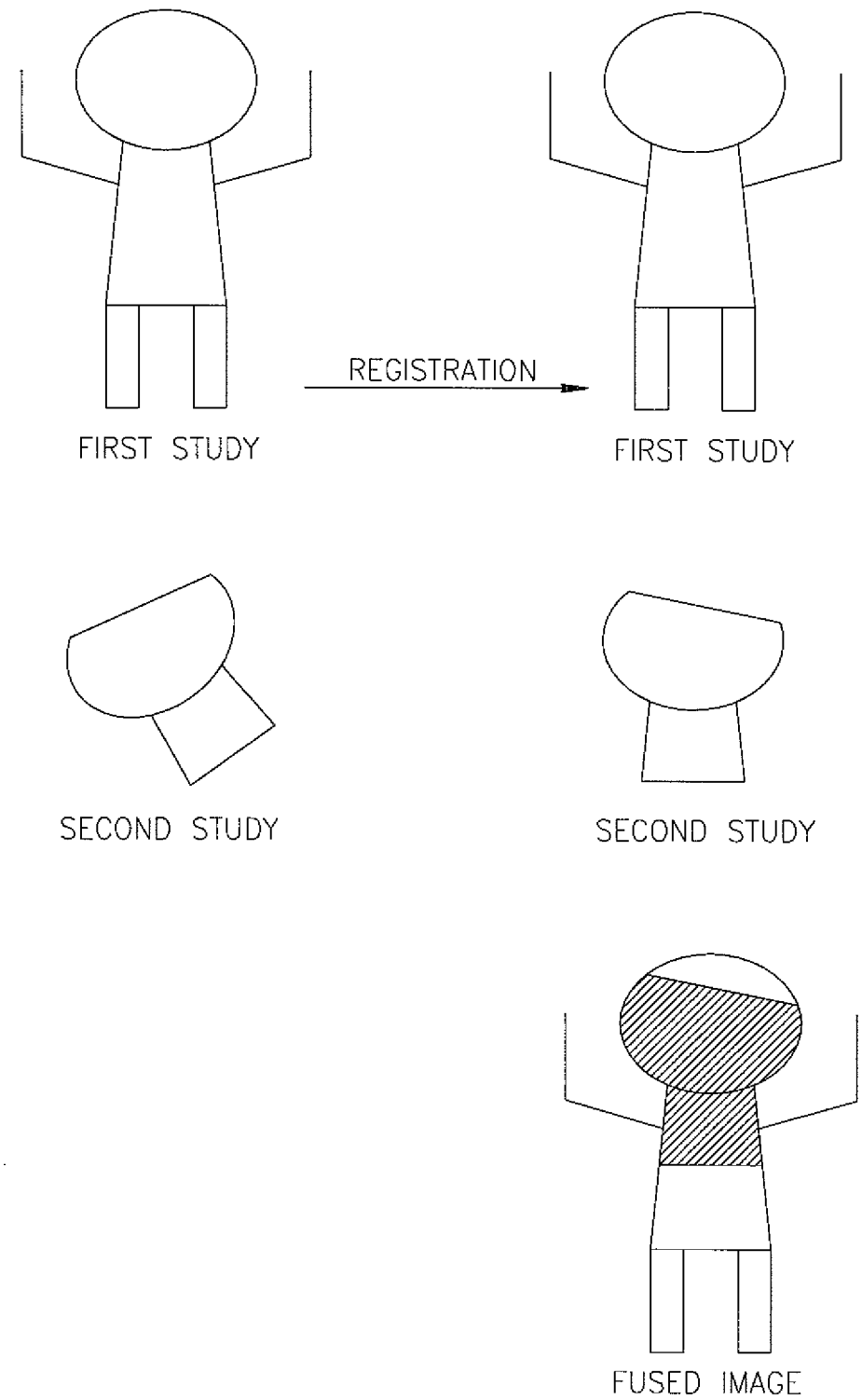
FIG. 1 is a schematic illustration of a registration process, according to an exemplary embodiment of the invention.

The description below relates to procedures and workflow for registering radiological data sets for high-throughput diagnostics, assisting in comparing them. FIG. 1 illustrates schematically two arbitrarily oriented data sets are registered.

The specifications refer to CT data sets as an example, but other radiological data sets such as MRI, PET, SPECT and registration of combinations such as CT/MRI, CT/PET or CT/PET/MRI may be provided as well, possibly requiring other registration methods.

Exemplary Equipment

In an exemplary embodiment of the invention, a radiology reading workstation of the kind used for high-throughput diagnosis is used to perform the registration and view the results. Optionally this workstation is a conventional personal computer, possibly with a display adapted for gray scale dynamic range and fidelity suitable to render radiological data sets. Unless otherwise specified, this kind of workstation is assumed in the rest of the application.

Optionally the workstation is linked to an archiving and communications system (PACS) where the data sets are stored; optionally the data sets are in a different database or in loose organizations; optionally the data sets are stored on portable media such as CD, DVD, tape or USB flash memory.

Exemplary Workflow

In exemplary embodiments of the invention, the workstation is used to register automatically a plurality of data sets of a patient, so that the registration time is approximately the same as the data sets retrieval overhead, for example, within 200%, 100%, 50% and/or 20% thereof or intermediate or smaller values. Alternatively or additionally, the registration time is controlled to be less than 30 seconds, less than 15 seconds, less than 7 seconds or intermediate values.

Figure 2:
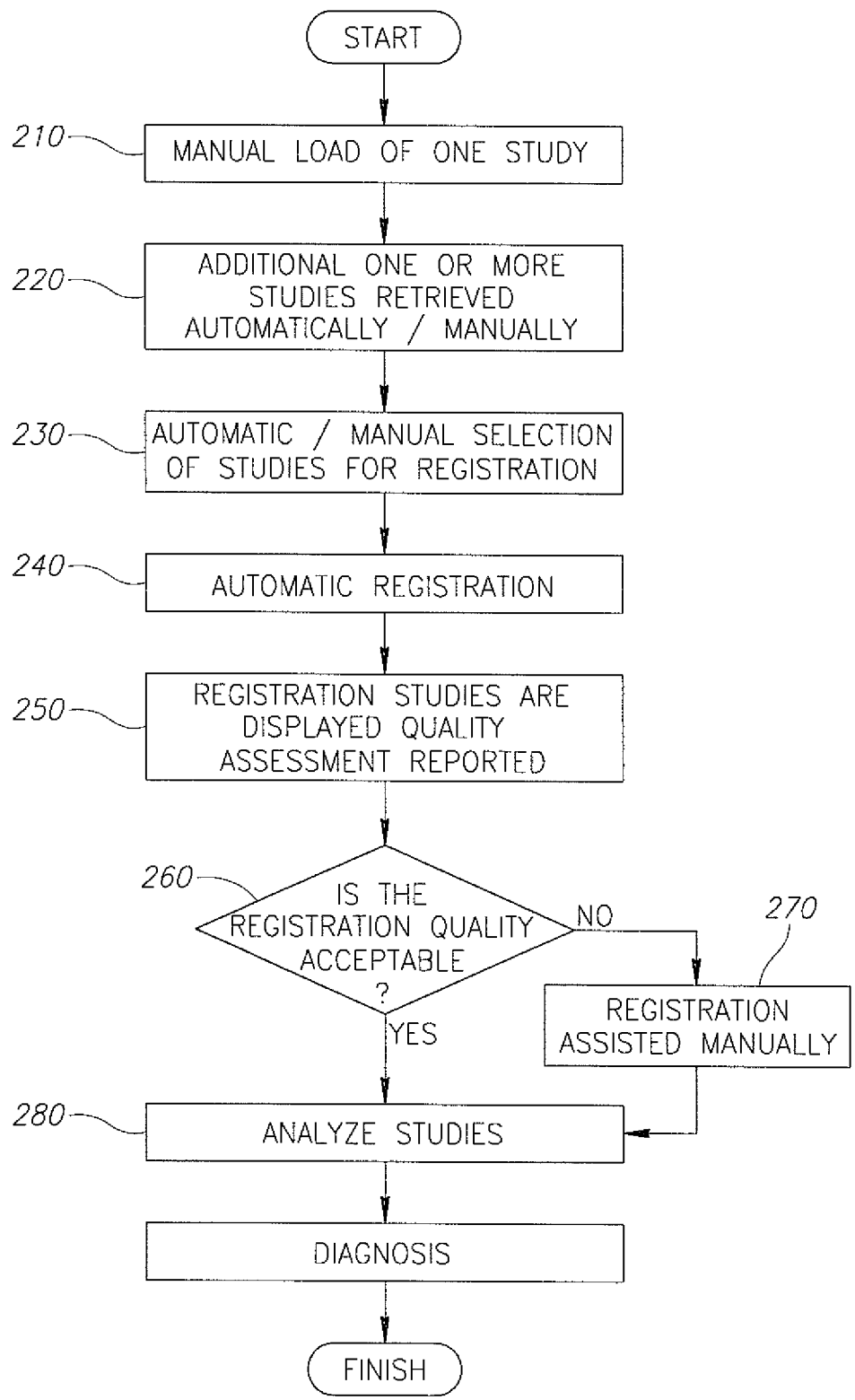
FIG. 2 is a flowchart illustrating an overview of the operational workflow in high throughput radiology reading, according to an exemplary embodiment of the invention.

FIG. 2 illustrates an overview of the operational workflow of automatic registration and comparison of radiological data sets, in accordance with an exemplary embodiment of the invention.

In an exemplary embodiment of the invention, after a data set is loaded manually (210), at least one data set is retrieved automatically (220). The automatic retrieval is optionally responsive to the clinical procedure, studied body part, or other information associated with the data sets, such as dates or postures. Optionally, a set of rules is defined for selecting a reference data set given a current data set and optionally additional information (e.g., diagnosis), and may be dependent, for example, on a period of time which should elapse between the data sets.

Optionally the retrieved data sets for registration are selected automatically (230). Optionally at least one data set is selected following a manually selected one. Optionally the selection for registration is responsive to parameters similar to those used for retrieval.

Optionally the registration is activated automatically (240). The automatic registration activation is optionally responsive to the size of the data sets so that only fast matching is activated for a smooth workflow and/or to other factors, for example, the complexity of the data sets. Optionally the conditions for automatic activation are configurable, for example, to start only below certain data set size or number of data sets to be registered.

Optionally the registration may execute while the operator views or manipulates the data sets being registered. Optionally other data sets are retrieved while the registration is executing. Optionally other operations may be performed while the registration is executed, for example, storing previous data sets that were loaded.

In some exemplary embodiments of the invention, registered volumes of CT data sets, possibly immediately after to the completion of the registration, are presented simultaneously on the workstation (250). Optionally the data sets are presented in a multi-planar format wherein at least one of the volumes was transformed by the registration process to align with the orientation of another volume. Optionally a transformed data set also was re-sliced to match the planes of the other data set (MPR). Optionally all the data sets are re-sliced to match some other criteria, such as spacing between planes. Optionally the data sets are presented as rendered, substantially continuous, volumes.

In some exemplary embodiments of the invention, the registered data sets are presented in axial, coronal or sagittal orientation. Optionally the data sets are oriented along a determined, or selected, or an arbitrary axis. Optionally the volumes are presented side by side or at least partially merged ('fused'). Optionally the fused volumes are displayed with pseudo-colors to distinguish between regions of each volume.

In some exemplary embodiments of the invention, since there is a direct spatial relation between the registered data sets, they may be accessed and manipulated in a synchronized manner (280) so that an operation performed on a point or region in one data set will be applied on the corresponding point or region on another data set.

A partial list of examples is, one or more of which are optionally provided:

(a) Indicating a point in one volume will indicate or highlight the corresponding point in another volume.

(b) Moving or rotating one volume will move or rotate another volume accordingly.

(c) Scrolling through planes of one volume will scroll through corresponding planes in another volume, showing the corresponding planes together.

(d) Re-slicing one volume in a new orientation can slice another volume according to that orientation and optionally with the same spacing (MPR).

(e) Annotations that are performed at a location of one data set will annotate the substantially corresponding location on another data set.

(f) A measurement performed on a region of one volume will measure also the corresponding region of another volume.

(g) A segment defined on one volume will define the corresponding segment at another volume.

(h) Applying image operations, such as filters, on one volume will apply the same filter on another volume at the corresponding spatial points.

In some exemplary embodiments of the invention, selected volumes are accessed and manipulated while the rest remain in their last state. Optionally, manipulations applied to selected volumes may be applied subsequently to other registered volumes.

In some exemplary embodiments of the invention, the registration of volumes may relate to only a certain portion of the volume. Optionally the portion comprises a particular anatomical structure. Optionally the portion is selected automatically by some criteria, such as density range or locality for example, skull. Optionally the portion is selected according to methods described in a Co-pending Israeli application No. 179581 filed on Nov. 26, 2006, entitled 'Spine labeling' the disclosure of which is incorporated herein by reference. This application describes a process of automated or semi-automated labeling which is optionally provided to enhance diagnosis ability at a reading workstation.

The portion to take part in the registration may also be selected using a computer-assisted method, in which, for example, a user indicates key points and, in response, an automated circuitry defines a region. Optionally the portion is selected manually. See (320) in FIG. 3. Optionally the portion taking part in the registration comprises of a plurality of regions.

Using only a portion of the volume may be useful to eliminate irrelevant parts that will consume processing time and/or parts that are deformed or such that they will hamper the registration or lead to inappropriate registration. For example, if the head is inspected, the neck and below parts may be in a different posture between the scans, and if they are taken into account, they might spoil the registration, at least as the head is concerned as the region of interest.

Registration Quality Assessment

In some exemplary embodiments of the invention, the quality of the spatial registration is assessed, to determine the degree of spatial matching between the two data sets. In exemplary embodiments of the invention, the quality of registration is assessed by a function. Typically, and at least for stationary or rigid body parts the matching is satisfactory, with posture, breathing or disease-inflicted differences being relative small and thus only marginally affecting the quality assessment. Optionally, the quality function is designed to ignore tissues that are not of interest or to allow tissue that is expected to move, to move without affecting the quality function (e.g., bowel movement). An exemplary formula that may be used in assessing the registration quality is described below. Optionally the assessment is invoked automatically. Optionally the assessment process provides a degree of the assessed quality. Optionally the degree indicates a result relating to 'success', 'failure' and 'unsatisfactory'. Optionally other scores are provided, for example numerical values on a given scale, e.g., 1-5.

When the reported assessed quality of the registration is not acceptable for the operator (260), or the expected time consumed by the automatic registration is too long (for example due to significantly dissimilar anatomies such that no match is obtained automatically or very large data sets) in some exemplary embodiments of the invention, the registration may be assisted manually (270) by the operator. Optionally the operator may use the workstation facilities to move, rotate or scale a volume relative to another until a satisfactory visual match is achieved. Optionally or alternatively, a plurality of corresponding points ('landmarks') are indicated in at least two volumes and a process is invoked to spatially transform a volume so that the corresponding points are spatially close to a certain degree.

In some exemplary embodiments of the invention, after a manually assisted registration, an automatic registration may be activated to the pre-registered data sets. This may improve or speed up a subsequent registration since the previous manually assisted registration may establish a better starting position for the next one. The manually assisted registration may be optionally assessed by the quality assessment process (described below).

In some exemplary embodiments of the invention, the mismatch between the registered volumes is highlighted, for example, by color or texture. The mismatch may be quantified, for example, by some volumetric value or ratio. This may be useful to see variations between the data sets and may also highlight deformations or features changes due to a disease.

Storage

Optionally the registration results are stored in a relevant database on a server such as in PACS or on other equipment such as CD.; optionally they are stored in DICOM format. Optionally, other formats may be used. Optionally, upon retrieval of the data sets prior to registration the system checks whether registration data (e.g., a transform function and/or areas that are ignored or enhanced during registration) for the two volumes of interest is already present on the server from previous reading(s) of the data sets; optionally if the registration data is available system skips the registration calculations and uses this data, Pre-Processing In some exemplary embodiments of the invention some preparatory pre-processing of the data sets is optionally performed before the actual registration so that the registration may work on data arranged for its operation. Optionally a copy of the data sets is pre-processed, for example, to preserve the original data sets.

Figure 3:
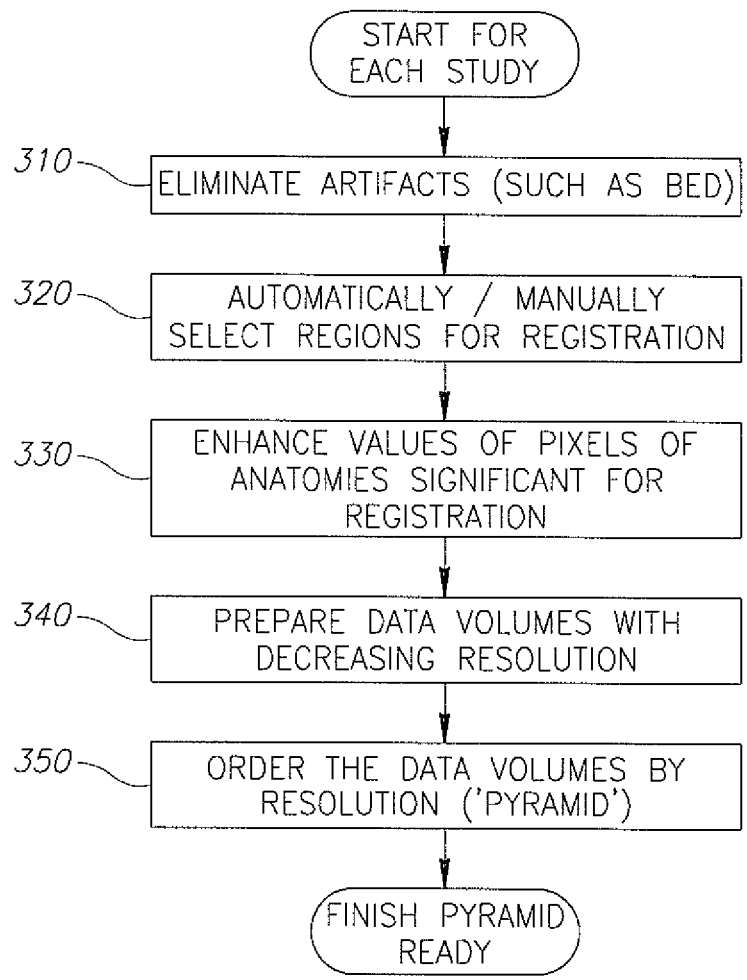
FIG. 3 is a flowchart illustrating an overview of pre-processing for a stepwise registration, according to an exemplary embodiment of the invention.
Figure 4:
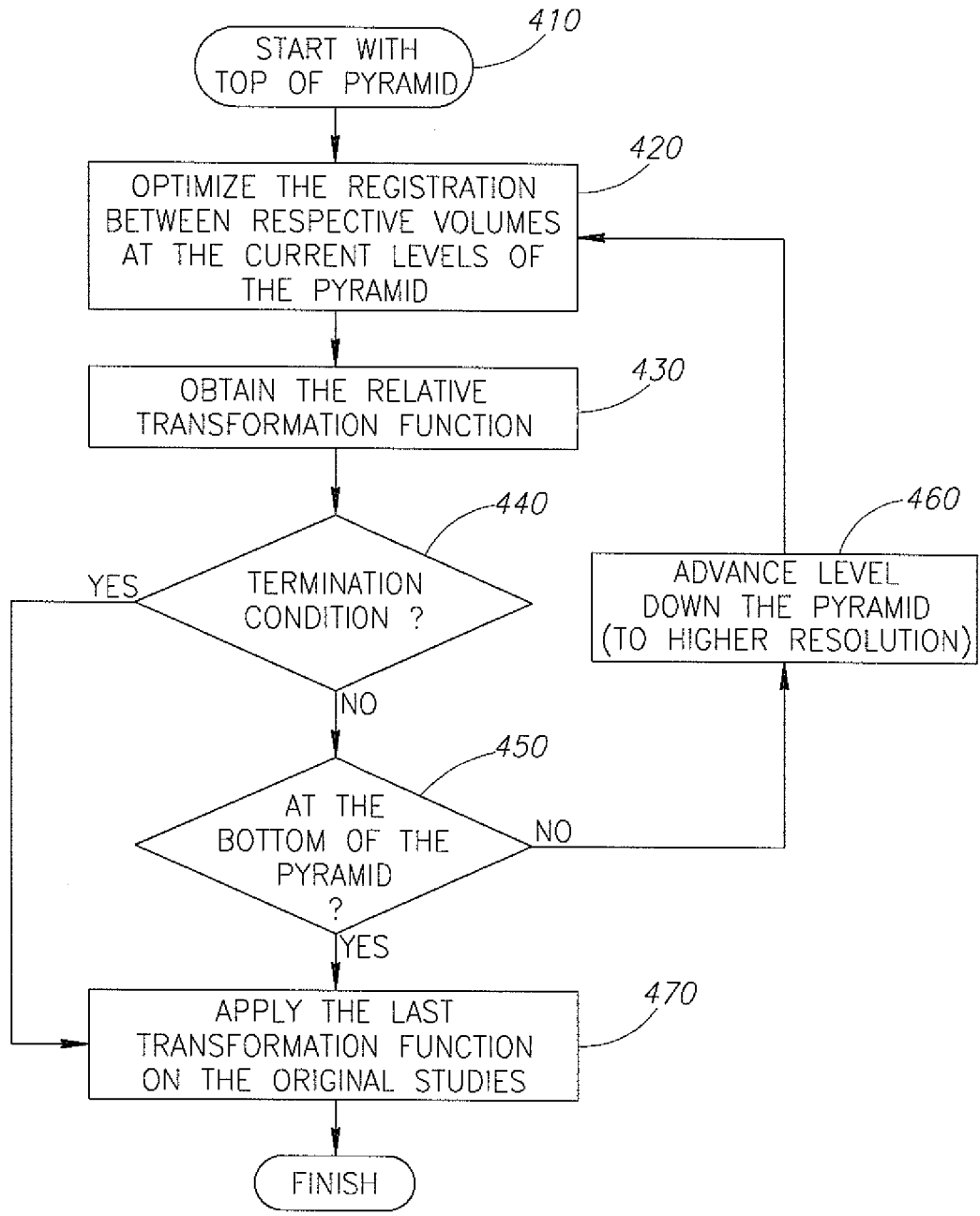
FIG. 4 is a flowchart illustrating a process of obtaining a stepwise matching from a pyramid of data set volumes in varying resolutions, according to an exemplary embodiment of the invention.

FIG. 3 illustrates an overview of the pre-processing for a stepwise registration and FIG. 4 illustrates an overview of the process of obtaining a stepwise registration from a hierarchy of data set volumes in varying resolutions ('pyramid').

CT Data Preprocessing

In exemplary embodiments of the invention, as an optional preprocessing, a volume of a CT data set is processed by at least one morphological filter that extracts the patient body and eliminates external objects or artifacts, such as the scanner bed. Optionally, for extracting the region of the body, a preliminary binarization of the data set is performed. Optionally the data set is binarized by thresholding; optionally the threshold is at a certain HU level. Optionally the binarization is function of the HU level or its neighborhood; optionally other binarization techniques are employed.

In exemplary embodiments of the invention, the body region is extracted by assuming that it is represented by the largest connected component in the binary images and it is kept substantially intact, while the residual components are eliminated (310) by subsequent erosion (a morphological process that eliminates pixels connected in a certain geometry).

Anatomical Emphasis

In an exemplary embodiment of the invention, registration gives a higher weight to some tissue over other tissue. In one example, the weighting of bony tissue (e.g., optionally not including the ribs, which may move due to weight gain or breathing) is higher than for soft tissue, due to lower expected degree of changes in the boney tissue. Optionally, this weighting is applied during registration, for example, using a look-up table. Alternatively or additionally, the weighting is applied by first pre-processing the images. Optionally, ribs (or other movable rigid tissues, such as bones connected by joints) are given a weight with respect to the whole rib moving as a unit, but not with respect to each voxel of the bone.

Optionally the pixel values (e.g. density) of hard components are increased. Optionally the pixel values of soft components are reduced. Optionally the data set's pixels values undergo a non-linear transformation with a contrast adapted to yield a larger discrepancy between values of bony components (in different data sets) relative to the discrepancy between the values of soft tissues (330).

In some exemplary embodiments of the invention, a portion of the bony components is adapted so that their respective discrepancy is reduced or eliminated (rather than enhanced), reducing or eliminating the contribution to the registration of certain regions. This operation may be useful in cases such as a substantial deformation in the body, or when the data sets are of different postures, such that only a certain region of interest of the body is consistent between data sets (e.g. the skull). Thus, in such cases, only the consistent region between the data sets will take a part in the matching. Optionally, the non-interest regions are accorded a weight of less than 30%, less than 20%, less than 10%, about 0% or intermediate percentages of the weight accorded to the region of interest.

In some exemplary embodiments of the invention, the value discrepancy for a part of the data set is enhanced irrespective of the hardness (e.g. density) values, as it may represent, for example, the region of interest. Optionally the discrepancy is responsive to anatomical structures, or to other factors. This may be useful to influence the matching to consider the region of interest more significant relative to other regions.

Volume Matching

In an exemplary embodiment of the invention, each data set appears in its frame of reference (FOR). Optionally, the FOR is stored in DICOM format. The registration is achieved by volumetric matching of at least two data sets and obtaining a transformation that between two (or more) FORs. Subsequently, this transformation is applied to the original data sets so that their volumes will substantially match each other in space; see FIG. 1 and (470) in FIG. 4. Optionally, the transformation is a non-deforming transformation. In some embodiments, the transformation is a deforming transformation.

Typically, two data sets are registered, but optionally more data sets may be registered. For example, one data set is taken as reference, the rest are each registered to it, and the respective transformation is subsequently applied to the respective data set. This may be useful, for example, to show changes in size and/or shape of a tumor over time, with previous data sets shown as ghost or color line overlays.

In an exemplary embodiment of the invention, the matching procedure substantially minimizes a cost function that reflects a volumetric disparity between the elements of the data sets, such that when the function is decreased the mismatch between the data sets elements is decreased.

Optionally, when both data sets being registered are CT scans, the cost function is defined as the sum of the absolute values of the discrepancies between voxel levels (e.g. densities) across the intersection of the volumes, normalized by the volume of the intersection. In an exemplary embodiment of the invention, a transformation function is defined that maps a voxel in one data set to a voxel in another data set. The cost function is defined as the sum of the absolute values of the discrepancies between voxels levels across the intersection of the new (transformed) volume and the other volume, normalized by the volume of the intersection, according to the following Eq. 1:

$$f[T] = \frac{1}{\Omega(I)} \sum_{i \in I} |p_i - q_j|, \quad \text{(Eq. 1)}$$

so that $T(i) = j$ where I is the domain of the intersecting volumes and $\Omega(I)$ is the volume of the intersection; $p_i$ and $q_j$ are the values of voxels of the two volumes in the intersection, respectively; T is the transformation function; and f[T] is the cost function.

Optionally, the cost function is defined as proportional to Mutual Information (MI) between the data sets. Optionally, the cost function depends on the correlation between data sets. In other embodiments of the invention, additional forms of the cost function can be used.

In exemplary embodiments of the invention, the minimization of the cost function is performed by a downhill simplex procedure iterated while the cost variation across the simplex is larger than a certain value or ratio. Optionally, but not restricted to, the default ratio is 1%. Alternatively or additionally, other minimization methods known in the art may be used.

Optionally the transformation function transforms in all the 7 degrees of freedom, namely, 3 translational, 3 rotational and one for scaling. Optionally, the function transforms in a subset of the degrees of freedom, for example translations only.

Optionally, the matching is performed with respect to partial degrees of freedom (e.g. translations without rotations or scaling or otherwise) and subsequently, starting with the resulting volumes, it is repeated with respect to more or other degrees of freedom. Optionally this approach simplifies or speeds up the registration. For example, a matching procedure may use only translational and scaling degrees of freedom, which may be relatively simple and fast relative to employment of all 7 degrees, to establish a coarse match. Then, starting with the close match position, the registration may employ the 3 rotations degrees of freedom, which, again is simple relative to using all degrees. Optionally a final refinement may use all the degrees of freedom from almost matched positions, i.e. matching positions which are sufficiently or satisfactorily matched. Optionally, the initial registration is performed at a lower resolution, for example, as described below.

In exemplary embodiments of the invention, responsive to a quality assessment (described later), the registration may be repeated using different parameters (e.g. different transformation function parameters, modified enhancement of the bony components, or constraints such as degrees of freedom) to achieve a better match with respect to the elements of the data sets.

Step-Wise Registration (Pyramid)

In some embodiments of the invention, matching the original data sets (after pre-processing) may be too complex and/or require too much memory and/or consume too much time since such calculations involve a large amount of data, where the data of each volume originally has no spatial relationship with the other volume. An alternative approach, which may be simpler and/or faster, is to divide the matching into sub-steps so that each sub-step involves matching only an incremental amount of data where that data is already partially matched. Optionally, the incremental amount of data is small relative to an unmatched data. The data for such an approach may be, for each volume, a collection of respective volumes in reduced resolutions, where the first step will be performed on the lowest resolution volume, and the next step will involve a higher resolution volume which improves the matching of the previous step, and so on.

In exemplary embodiments of the invention, the resolution of the images of at least two data sets is reduced to form a smaller volume of smaller spatial resolution. Optionally the resolution reduction is done by filtering and re-sampling. Optionally the filter is an averaging filter, or another low-pass filter or other filter to that effect. Optionally the resolution of volumes of the data sets is reduced by block-averaging in 3D with subsequent down-sampling (340). Optionally, the construction of a pyramid is used for pre-fetching low quality data, for example, for initial physician assessment and/or for registration while the rest of the data set(s) data is being retrieved. Optionally, the pyramid is prepared before diagnosis and fetching, for example, during or after data set acquisition.

In exemplary embodiments of the invention, the resolution reduction is done into a plurality of levels for optional multi-step registration as outlined above. Optionally the number of levels or the resolution reduction is determined according to the original resolution and is, for example, 3, 5, 7 or intermediate, smaller or larger levels. Optionally or additionally, the levels and resolutions are determined by the original volume. Optionally the levels and resolutions are determined by other factors such as a satisfactory accuracy or, optionally, the number of levels or resolution reduction is configurable or arbitrary.

In exemplary embodiments of the invention, the contrast resolution is changed by normalizing the gray-level values to a predetermined range. Optionally, the contrast resolution is varied across the pyramid.

In exemplary embodiments of the invention, the resulting volumes of each data set are ordered by the resolution reduction level to form a hierarchy ('pyramid') of 3D volumes of decreasing data volume and spatial and/or contrast resolution, the volume of lowest resolution considered the 'top' of the pyramid (350).

In exemplary embodiments of the invention, the volumes at a respective pyramid level are sequentially registered, level by level, from top (lowest resolution) to bottom (highest resolution).

Since the volumes at or around the top of the pyramid contain a relatively small amount of data, they are optionally registered by an exhaustive search through the parameter space, for example, by using all the 7 degrees of freedom. In some cases, it should be noted, a degree of deformation may be allowed, for example, for individual voxels or for identifiable groups of voxels. Exemplary identifiable groups may be such as rib or ribs that do not match due to different breathing levels between the data sets, or slight orientation of the skull relative to the shoulders, or an arm or leg relative to the torso, and other similar cases Optionally or alternatively, a morphing (warping) operation is used to decrease the deformation between the data sets.

FIG. 4 illustrates a sequence of operations to obtain a stepwise matching from a pyramid of data set volumes in varying resolutions, in accordance with an exemplary embodiment of the invention. The basic sequence comprises:
  (a) The data volumes at the top of the pyramid (410) are registered.
  (b) A spatial transformation is obtained (430).
  (c) The volumes at another level down the pyramid (460) are transformed accordingly to new starting positions and are subsequently registered (420).

In exemplary embodiments of the invention, once the last registration step is performed the last transformation function is obtained. By applying that transformation on the original data sets (450) a spatial registration of the original two data sets is achieved.

Optionally the last step is at the lowest level in the pyramid, that is, the highest resolution (450). Optionally the last step is determined responsive to a high quality coefficient, or once a satisfactory matching is achieved. Optionally other criteria may be used such as the intersection volume that may reflect a satisfactory match (440).

In exemplary embodiments of the invention, registration methods known in the art are applied to the above methodology, for example, being modified to include different weighting for different tissue types. Optionally, the differential weight of different tissue types is implemented using a lookup table mapping weights to tissue types.

Exemplary Matching Quality Assessment

In exemplary embodiments of the invention, the quality of a registration procedure may be estimated by calculating the normalized correlation coefficient, according to the following Eq. 2:

$$NC[T] = \frac{\sum_i p_i q_{T(i)}}{\sqrt{\sum_i p_i^2 \sum_i q_{T(i)}^2}}, \quad (\text{Eq. 2})$$

$$i \in I$$

Where I is the domain of the intersecting volumes; $p_i$ is a value of a voxel of a data set and $q_{T(i)}$ is a respective voxel of a transformed data set; T is the transformation function that maps voxels of one data set into the region of the other volume; and NC[T] is the normalized correlation coefficient.

Registration Refinement

In exemplary embodiments of the invention, two or more data sets are globally registered (e.g. by bones), optionally as described above. A volume about a region of interest (ROI) in one data set is selected and, optionally, a characteristic zone or point is indicated within the ROI. Subsequently, based on the selected ROI and optional zone or point, a corresponding volume in other one or more data sets is determined and registered, automatically or upon a user interaction. In exemplary embodiments of the invention, the ROI is a soft tissue or organ, so that such a local registration (refinement) allows registering organs that moved between data sets, such as due to breathing, or that varied such as due to tumor development or relapse.

In exemplary embodiments of the invention, if the refinement registration is not acceptable, it is repeated iteratively until a satisfactory match is achieved.

In exemplary embodiments of the invention, a satisfactory refinement convergence is determined according to a predefined threshold and/or a relative threshold (e.g. 10%) of the volume difference between the sub-volumes. Optionally or alternatively, a convergence is determined based on an estimation of the match (difference) between corresponding characteristics zone and/or points in the data sets, such as by predefined threshold and/or relative threshold. Optionally or alternatively, the refinement converges successfully when the transformation between the corresponding sub-volumes converges within a limit. Optionally, the convergence is determined by at least one element of the transformation, such as translation, rotation or scaling. Optionally or alternatively, the match is determined visually by the operator.

In exemplary embodiments of the invention, the ROI and/or characteristic point are selected by a user, for example, by a mouse. Optionally or alternatively, the ROI and/or the point are determined automatically, or semi-automatically, for example, a characteristic point is identified by contrast or shape within an indicated ROI.

Unless otherwise specified, and without limiting the generality of the descriptions and/or discussions below, one data set will be referred to as a first data set, and the other one as a second data set, wherein the second data set may refer to one or more other data sets.

Figure 5:
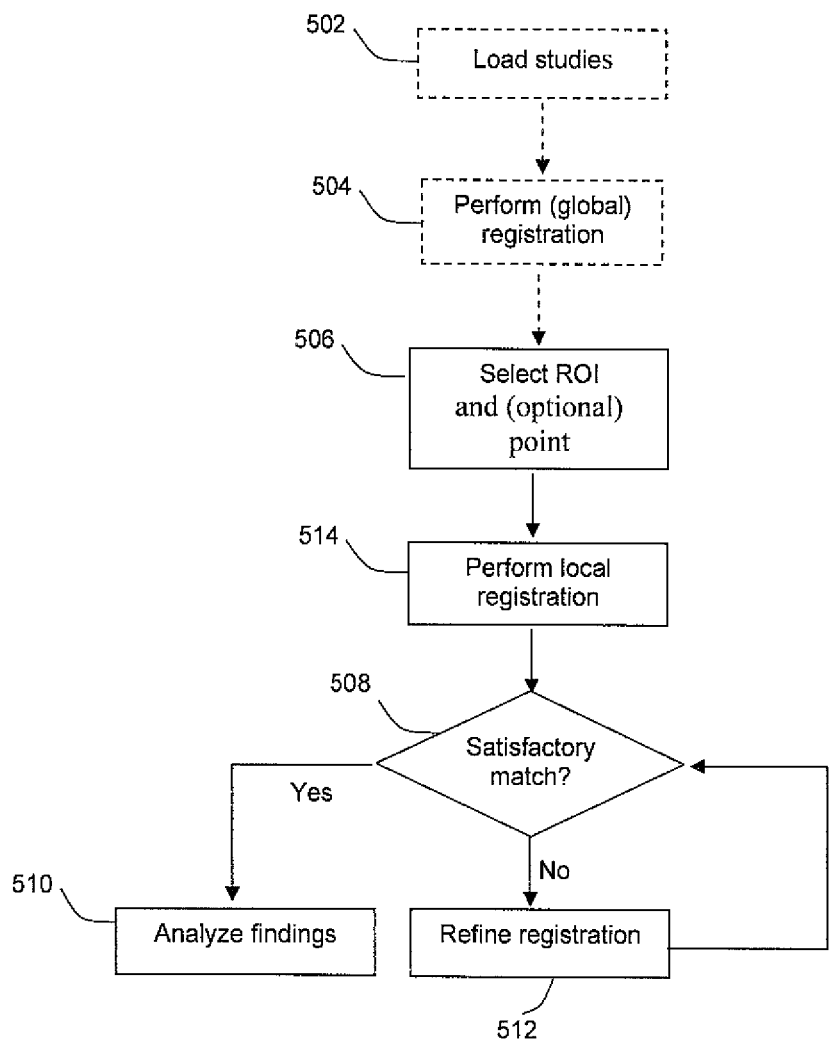
FIG. 5 is a flowchart illustrating an overview of a registration refinement, according to an exemplary embodiment of the invention.

FIG. 5 is a flowchart illustrating an overview of a registration refinement, according to an exemplary embodiment of the invention. Preliminary, optionally if global registration was not performed or not available, the first and second data sets are loaded (502) and optionally displayed as described above. The data sets are spatially registered, optionally as described above (504).

In exemplary embodiments of the invention, when global registration is available, a local refinement is performed. A volume about the ROI, with an optional characteristic point zone or point, is selected in the first data set (506), for example, by browsing through planes of the volume until one (or more) planes are displayed on a screen. Consequently, the assumed corresponding volume in the second data set is displayed, and registered with the ROI of the first data set (514), and the matching between the two volumes is determined or assessed (508). If the match is satisfactory, the refinement is finished and the respective regions may be analyzed and/or diagnosed (510). Otherwise, a registration refinement is iterated (512), optionally several times (step-wise), until a satisfactory match is achieved (or a limit on the number of repetitions is reached).

In exemplary embodiments of the invention, only the first data set is loaded where the ROI and optional characteristic zone is indicated. Optionally, the second data set is loaded and displayed upon registration. Optionally or alternatively, the second data set is registered without concurrent display, such as for later review.

In exemplary embodiments of the invention, the registration refinement quality (e.g. in terms of overlapping of the volumes about the ROI) may be affected by one or more of the following conditions:

(a) The global registration, as described before, is satisfactorily performed.

(b) The local anatomy about the ROI does not change much between the two data sets.

For example, a lung nodule may be present in one data set and not on the other but the overall configuration of the tissues about the ROI of both data sets is similar.

(c) The displacement of the soft tissues between the two data sets is not large, that is, they are about the same location relative to the skeleton. For example, the tissues are connected to, or constrained by, the skeleton and do not change their shape or size or location significantly between scans (e.g. holding breath while scanning). In accordance with exemplary embodiments of the invention, the iterative refinement as illustrated schematically in FIGS. 6A, 6B and 6C and with reference to FIG. 5.

Figure 6A:
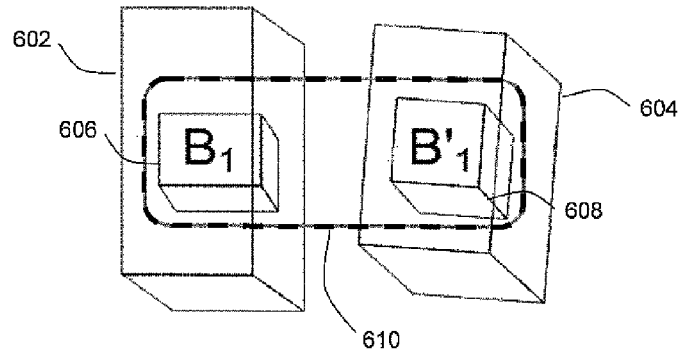
FIG. 6A schematically illustrates two data sets and the respective two sections about a region of interest, according to an exemplary embodiment of the invention.
Figure 6B:
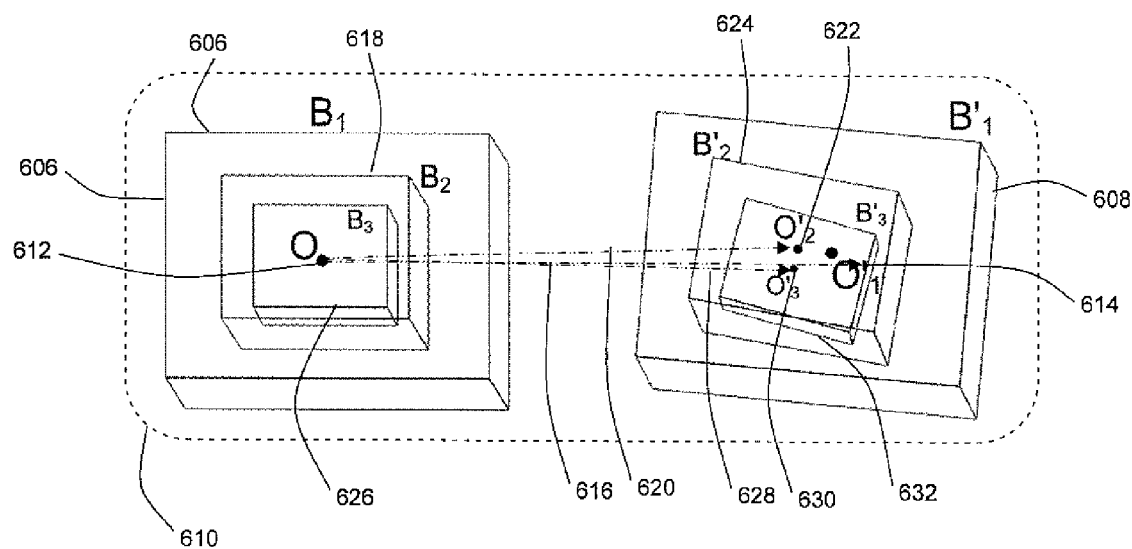
FIG. 6B schematically illustrates a two-step registration refinement about a region of interest in respective sections of two data sets of FIG. 6A, according to an exemplary embodiment of the invention.
Figure 6C:
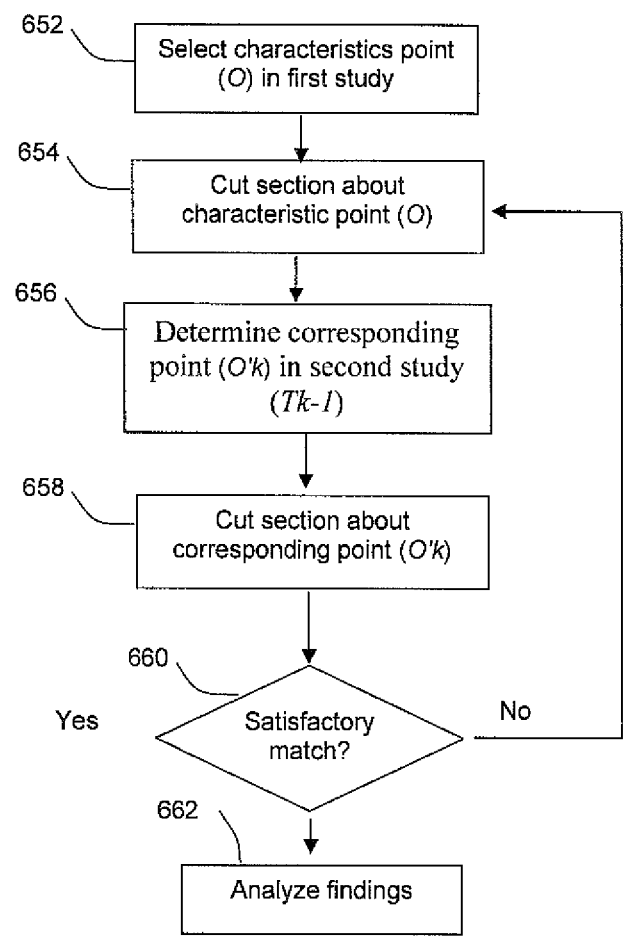
FIG. 6C is a flowchart illustrating a step-wise registration refinement, according to an exemplary embodiment of the invention.

FIG. 6A schematically illustrates two data sets 602 and 604 and the respective two sub-volumes 606 and 608 ($B_1$ and $B'_1$) about a region of interest, while FIG. 6B schematically illustrates a two-step registration refinement about respective sub-volumes 606 and 608, according to an exemplary embodiment of the invention. An auxiliary dotted frame 610 illustrates a relation between FIGS. 6A and 6B. FIG. 6C is a flowchart illustrating a step-wise registration refinement respective to FIGS. 6A and 6B, according to an exemplary embodiment of the invention.

In exemplary embodiments of the invention, a characteristic anatomic point or localized pathology (and/or well defined zone) 612 (O) is identified within the ROI in first data set 602 (652). A sub-volume 606 ($B_1$) of given dimensions is 'cut' out of data set 602 about point 612 (O), that is, only (or mostly) section 606 ($B_1$) is taken into account (654) for subsequent operations, discarding the rest of the data set. Optionally, sub-volume 606 is somewhat larger than the estimated or known volume of the pathology or its surroundings because the corresponding ROI in the second data set may be found somewhat away from what is found or expected by the global registration. Optionally or alternatively, the region is determined to provide a sufficient volume for matching so that some non-matching voxels will not distort the registration. For example, if the organ or pathology dimensions are about 20×20×20 mm then the sub-volume may be about 30×30×30 mm.

Using a transformation 616 ($T_0$), a point 614 ($O'_1$) in second data set 604 corresponding to point 612 (O) in first data set 602 is determined (656) (i.e. k=1). Optionally, the determination is according to the global transformation as described above, e.g. Eq. 1. A section 608 equal or similar in dimensions to section 606 (B'$_1$) is cut about corresponding point 614 (O'$_1$).

If a satisfactory (such as described above) match is found between points 612 (O) and 614 (O'$_1$) (660) then the refinement is over (finished) (662) and the respective regions may be analyzed and/or diagnosed.

Otherwise, a first step of registration refinement is performed (k=2). Section 606 (B$_1$) is further divided into an optionally smaller section 620 (B$_2$) (654), and a transformation 620 (T$_1$) is determined (656) to find a point 622 (O'$_2$) with a possibly better match with point 612 (O). The transformation is determined, for example, by a matching as describe above, e.g. with respect to Eq. 1. Optionally, unlike the global registration, the relative weight of the voxels is not modified in the determination of the transformation. Subsequently, region 608 (B'$_1$) is cut (658) into a section 624 (B'$_2$) of a similar volume as 618 (B$_2$).

If a match is not found between points 612 (O) and 622 (O'$_1$) (660), then a next step of registration refinement is performed (k=3). Section 618 (B$_2$) is further cut into an optionally smaller section 626 (B$_3$) (654) and a transformation 628 (T$_2$) is determined (656) to find a point 630 (O'$_3$) with a possibly better match with point 612 (O). Subsequently, region 624 (B'$_2$) is cut (658) into a section 632 (B'$_3$) of a similar volume as 626 (B$_3$).

In exemplary embodiments of the invention, the transformation that yields the best match (typically the last step, T$_n$) is stored, in a local computer, server or PACS system. Optionally, the ROI coordinates and/or data subsets are stored. The stored transformation or the stored sections may be recalled later without performing a registration refinement, but, rather, only one transformation T$_n$. Optionally or alternatively, the coordinates of the registered ROI sections within a data set are stored in the first and/or second data set and may be later recalled for immediate analysis and/or diagnosis.

Other Methods

In exemplary embodiments of the invention, the registration may comprise other methods, for example, Zernike moments, inertia-like moments, or other methods of the art.

Examples

In accordance with exemplary embodiments of the invention, two data sets are registered using a matching procedure as described above, assuming the intersection between the two 3D volumes is sufficiently large to include enough significant voxels (usually, but not restricted to, about 25% of the volume).

For illustrative example, using a personal computer based on Pentium 4 Xeon 2.8 GHz running the Windows XP system (respective commercial terms) the calculation time for a registration of two data sets of a substantially medium size (~350 slices) was approximately 2 seconds, and approximately 5 seconds for a substantially large size (~800 slices). The calculation time is typically responsive to the properties of the computer system, such as clock rate, amount and organization of memory, acceleration or parallelism hardware, and the number of processing units. A radiology reading workstation may be characterized, in addition or alternatively to technical specifications, by the diagnosis throughput it allows. An example is approximately 5 patient studies per hour for chest/abdomen stored data sets, or 5-15 minutes per study depending on the complexity of the case, but these numbers may vary also depending on the radiologists and the clinic. In an exemplary embodiment of the invention, the workstation is provided with software that is designed to facilitate high-throughput diagnostics, for example, software that provides a radiologist with a list of data sets to be read and records his reports on each study in turn. The numbers above show that the registration time is small relative to the overall diagnosis time, while the registered data sets may facilitate a faster and possibly better diagnosis.

General

Systems, methods and graphical user interface (GUI) according to exemplary embodiments of the invention rely upon execution of various commands and analysis and translation of various data inputs. Any of these commands, analyses or translations may be accomplished by software, hardware or firmware according to various embodiments of the invention. In an exemplary embodiment of the invention, machine readable media contain instructions for registration, display and/or user interaction. Such instructions may be, for example, loaded into a memory of the work station and executed by a processor thereof.

In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features. Alternatively and additionally, portions of the invention described/depicted as a single unit may reside in two or more separate physical entities which act in concert to perform the described/depicted function. Alternatively and additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. The scope of the invention is limited only by the following claims.

The invention claimed is:

1. A method for a rapid automated presentation of at least two radiological data sets of a patient, comprising:
   (a) loading a current dataset depicting at least one anatomical region of a patient;
   (b) automatically retrieving at least one prior dataset depicting said at least one anatomical region from a database;
   (c) automatically registering said dataset and said at least one prior dataset in 3D space, by:
      (i) selecting a first point in one of said current dataset and said at least one prior dataset and identifying a first region of interest around the first point;
      (ii) identifying an additional point in another of said current dataset and said at least one prior dataset, corresponding to the first point according to a transformation between the datasets, and identifying an additional ROI around the additional point; and (iii) performing an automatic volumetric registration of the said current dataset and said at least one prior dataset in 3D space according to a volumetric match between the first ROI and the additional ROI;

(iv) assessing a quality of the volumetric match between the first ROI and the additional ROI;

(v) if the quality of the match has not achieved a satisfactory refinement convergence, identifying a new first ROI around the first point, of different size, location, or both than the previous first ROI, identifying a new additional point according to a transformation corresponding to the volumetric registration, identifying a new additional ROI around the new additional point, performing an automatic volume registration according to a volumetric match between the new first ROI and the new additional ROI, and assessing the quality of the volumetric match between the new first ROI and the new additional ROI; and (vi) repeating (v), and stopping the repeating when the quality of the match achieves a satisfactory refinement convergence; and (d) concurrently presenting matching anatomical regions in each said data set.

2. The method of claim 1, wherein said automatically registering is activated automatically, and is performed while said current dataset is presented to a user.

3. The method of claim 1, wherein said automatically registering comprises re-slicing at least one of said current dataset and said at least one prior dataset, said concurrently presenting is performed based on said re-slicing.

4. The method of claim 1, wherein said concurrently presenting comprises presenting a fusion of said current dataset and said at least one prior dataset.

5. The method of claim 1, wherein said concurrently presenting is performed according to a member of a group consisting of: presenting both said matching anatomical regions as MPRs, presenting a slice on one of said current dataset and said at least one prior dataset and a corresponding MPR on another of said current dataset and said at least one prior dataset the second dataset, presenting a slice of one of said current dataset and said at least one prior dataset and a closest respective slice on another of said current dataset and said at least one prior dataset second dataset, and presenting a corresponding reference point on both one said current dataset and said at least one prior dataset so as to present an arbitrary plane of one of said current dataset and said at least one prior dataset containing the reference point and another arbitrary plane of another of said current dataset and said at least one prior dataset containing the corresponding transformed reference point.

6. The method of claim 1, wherein said concurrently presenting is performed on a radiological reading workstation suitable for high-throughput radiological display.

7. The method of claim 1, wherein said automatically registering and concurrently presenting are performed in a period of the order of or less than a period required for a retrieval of said current dataset and said at least one prior dataset.

8. The method of claim 1, wherein said current dataset and said at least one prior dataset comprise a member from a group consisting of a computerized tomography (CT), magnetic resonance imaging (MRI), positron emission tomography (PET), Single photon emission computed tomography (SPECT) or ultrasound (US) scans.

9. The method of claim 1, further comprising:
(a) assessing the quality of said registration; and
(b) reporting a score indicative of registration quality according to said assessment.

10. The method of claim 1, wherein said registered data sets are presented as rendered volumes.

11. The method of claim 1, wherein said automatic registering comprises:
(a) manipulating one of the at least two data sets; and
(b) automatically applying the manipulation to a substantially corresponding location in another of the at least two data sets.

12. The method of claim 1, further comprising performing a manual intervention for registration after said automatic registering.

13. The method of claim 1, comprising selecting in at least one volume a participating portion that will take part in the registration.

14. The method according to claim 13, wherein the participating portion is determined automatically.

15. The method of claim 1, wherein said registering comprises matching between voxels of a first of said current dataset and said at least one prior dataset and respective voxels of a second of said current dataset and said at least one prior dataset while giving greater weight to matching between voxels of one tissue type than to matching between voxels of another tissue type.

16. A method according to claim 15, wherein said voxels are manually mapped as of said tissue type.

17. The method according to claim 15, wherein said matching comprises identifying at least one anatomical structure in said current dataset and said at least one prior dataset and mapping said tissues type and the another tissue type according to the at least one anatomical structure.

18. The method of claim 1, wherein said automatic registering comprises processing at least one of said current dataset and said at least one prior dataset to yield a series of data volumes differing in at least one of a spatial resolution and a color resolution, and performing consecutive intermediate spatial matching steps on said data volumes, using a data volume of increasing resolution at each consecutive step.

19. The method of claim 18, wherein performing the spatial matching steps comprises employing one or both of a different number of degrees of freedom and a different type of degrees of freedom for different steps.

20. The method of claim 19, wherein the different steps comprise a first step of performing matching on a lower resolution data volume and a second step of performing matching on a higher resolution data volume, the first step using at least one translation degree of freedom, and the second step using at least one rotation degree of freedom not used for the first step.

21. A method according to claim 1, wherein concurrently presenting matching anatomical regions comprises slicing the at least two radiological data sets according to the volumetric registration so as to allow a concurrent presentation of matching anatomical regions in each respective data set.

22. A system for a rapid automated presentation of at least two radiological data sets of a patient, comprising:
an input unit for loading a current dataset depicting at least one anatomical region of a patient and automatically retrieving at least one prior dataset depicting said at least one Anatomical Region from a database;
a processing module configured for automatically registering said dataset and said at least one prior dataset in 3D space by:

(i) selecting a first point in one of said current dataset and said at least one prior dataset and identifying a first region of interest (ROI) around the first point;
(ii) identifying an additional point in another of said current dataset and said at least one prior dataset, corresponding to the first point according to a transformation between the datasets, and identifying an additional ROI around the additional point;
(iii) performing an automatic volumetric registration of the said current dataset and said at least one prior dataset in 3D space according to a volumetric match between the first ROI and the additional ROI;
(iv) assessing a quality of the volumetric match between the first ROI and the additional ROI;
(v) if the quality of the match has not achieved a satisfactory refinement convergence, identifying a new first ROI around the first point, of different size, location, or both than the previous first ROI, identifying a new additional point according to a transformation corresponding to the volumetric registration, identifying a new additional ROI around the new additional point, performing an automatic volume registration according to a volumetric match between the new first ROI and the new additional ROI, and assessing the quality of the volumetric match between the new first ROI and the new additional ROI; and
(vi) repeating (v), and stopping the repeating when the quality of the match achieves a satisfactory refinement convergence; and an imaging module for concurrently presenting matching anatomical regions in each said data set.

23. A method according to claim 1, wherein identifying an additional point in another of said current dataset and said at least one prior dataset, corresponding to the first point according to a transformation between the datasets, comprises identifying an additional point corresponding to the first point according to a global registration between said current dataset and said at least one prior dataset.

24. A method according to claim 22, wherein selecting the first ROI comprises selecting a region of soft tissue, and performing a refinement of the global registration comprises using degrees of freedom that allow a local registration between images of a soft organ that moved relative to surrounding tissue or changed between the current dataset and the at least one prior dataset.

25. A method according to claim 1, wherein each time (v) is done, the new additional point is identified according to a different transformation than that used to identify the additional point the previous time.

26. A method according to claim 1, wherein, before identifying the additional point in (ii), the two datasets are globally registered, and the transformation used to identify the additional point in (ii) is the transformation of the global registration.

\* \* \* \* \*